United States Patent [19]

Pidskalny et al.

[11] Patent Number: 4,954,161

[45] Date of Patent: Sep. 4, 1990

[54] HERBICIDAL COMPOSITION AND METHOD FOR SAFENING GRAMINEOUS CROPS AGAINST HETEROCYCLIC PHENYL ETHERS

[75] Inventors: Ronald S. Pidskalny, Edmonton; Paul G. Kneeshaw, Saskatoon, both of Canada

[73] Assignee: American Cyanamid Company, Stamford, Conn.

[21] Appl. No.: 294,855

[22] Filed: Jan. 9, 1989

[51] Int. Cl.$^5$ ................ A01N 43/56; A01N 43/76
[52] U.S. Cl. ........................................ 71/88; 71/90; 71/92
[58] Field of Search ................................ 71/88, 92

[56] References Cited

U.S. PATENT DOCUMENTS

| | | | |
|---|---|---|---|
| 3,882,142 | 5/1975 | Walworth et al. | 71/92 |
| 3,922,161 | 11/1975 | Walworth et al. | 71/92 |
| 4,130,413 | 12/1978 | Handte et al. | 71/90 |
| 4,170,464 | 10/1979 | Feeney | 71/92 |

Primary Examiner—Glennon H. Hollrah
Assistant Examiner—Kristina L. Konstas
Attorney, Agent, or Firm—John W. Hogan, Jr.

[57] ABSTRACT

A herbicidal composition of difenzoquat and a heterocyclic phenyl ether is safe for gramineous crops and effective in controlling grassweeds including wildoats and greenfoxtail.

7 Claims, No Drawings

HERBICIDAL COMPOSITION AND METHOD FOR SAFENING GRAMINEOUS CROPS AGAINST HETEROCYCLIC PHENYL ETHERS

BACKGROUND OF THE INVENTION

Wild oats and greenfoxtail are among the most troublesome weeds for farmers growing gramineous crops, such as wheat, barley, rye, triticale and other cereal crops. Full season competition can reduce crop yield significantly, resulting in serious economic losses in crop production. One of the most common practices for controlling wild oats and greenfoxtail is the use of postemergent selective herbicides. For example certain heterocyclic phenyl ethers are known herbicides which are effective against certain annual and perennial grass weeds. Unfortunately, these herbicides cannot be used in all gramineous crops, especially barley, because the herbicide injures the crop as well as controlling the weeds.

Therefore what is needed in the art is a herbicide which is effective against grass weeds, including wild oats and greenfoxtail, while protecting the gramineous crop from injury.

SUMMARY OF THE INVENTION

A method for protecting a gramineous crop from injury by a heterocyclic phenyl ether herbicidal compound of formula (I)

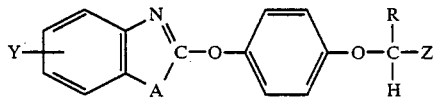

wherein
Y is hydrogen, halogen, $CF_3$, $NO_2$, CN, alkyl, alkoxy or alkylthio,
A is O, S, NH, or N-alkyl,
R is hydrogen or alkyl and
Z is a carboxylic acid, carboxylic ester, carbonamide, carbohydrazide, thioamide, nitrile, hydroxymethyl, acyloxymethyl, carbamoylmethyl, or sulfonyloxymethyl group.
by applying a difenzoquat salt to the heterocyclic phenyl ether in an non-phytotoxic antidotal amount.

Surprisingly, it has been found that the combination of difenzoquat and heterocyclic phenyl ethers controls undesirable plant species, such as wildoats and greenfoxtail, while protecting the gramineous crops from injury.

DETAILED DESCRIPTION OF THE INVENTION

Difenzoquat (or 1,2-dimethyl-3,5-diphenyl pyrazolium) is a known herbicide which selectively controls wildoats in gramineous crops. While other salts of difenzoquat may be employed, the methyl sulfate salt is preferred. Difenzoquat is not used to control greenfoxtail.

Heterocyclic phenyl ethers of formula (I)

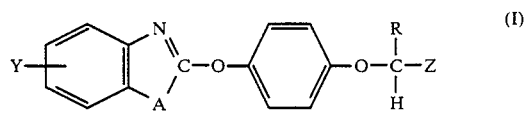

wherein
Y is hydrogen, halogen, $CF_3$, $NO_2$, CN, alkyl, alkoxy or alkylthio,
A is O, S, NH, or N-alkyl,
R is hydrogen or alkyl and
Z is a carboxylic acid, carboxylic ester, carbonamide, carbohydrazide, thioamide, nitrile, hydroxymethyl, acyloxymethyl, carbamoylmethyl, or sulfonyloxymethyl group
are known herbicides which are used in some gramineous crops, but are not used in all such crops because of their phytotoxicity.

Preferred heterocyclic phenyl ethers useful in the present invention include compounds of formula (I)

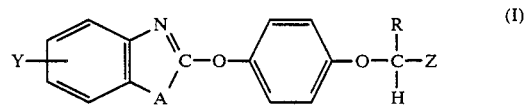

wherein
Y is halogen, $CF_3$, $NO_2$, $CH_3$, or methoxy;
A is O, S, or N—$CH_3$;
R is H or $CH_3$;
Z is $CH_2OH$ or $COOR_1$; and
$R_1$ is H, $C_1$-$C_6$ alkyl (optionally substituted with one or two halogen atoms and/or by OH), or phenyl (optionally sub- with one or two halogen and/or methyl groups).

Halogen preferably stands for fluorine, chlorine or bromine.

Fenoxaprop ethyl, a herbicide marketed by Hoechst under the trademark EXCEL, is an especially preferred heterocyclic phenyl ether of the present invention. Fenoxaprop ethyl is used in some gramineous crops, but cannot be used in barley because at herbicidally active rates fenoxaprop ethyl is phytotoxic to the barley crop.

The combination of a difenzoquat salt and a heterocyclic phenyl ether provides an unexpected benefit. The combination is safe in gramineous crops, including barley. The two herbicides are combined at rates of active ingredient which give control of the undesirable plant species, while sparing the crop from damage. Typical rates of application are about 0.500 kg/ha to 1.00 kg/ha of difenzoquat and about 0.050 kg/ha to 0.220 kg/ha of heterocyclic phenyl ether. In a preferred embodiment of this present invention, the herbicidal combination is applied so as to provide about 0.700 to 0.850 kg/ha of difenzoquat methyl sulfate and about 0.060 kg/ha to 0.100 kg/ha of fenoxaprop ethyl.

The present invention is prepared by tank mixing the two herbicides prior to delivering the herbicidal combination. This method of preparation is advantageous for immediate application to the field.

The present invention may also be prepared as a coformulation or package mix. A variety of commonly employed adjuvants may be added to the active ingredients of the herbicidal combination such as wetting/dispersion agents, surfactants, antifreezing agents and/or antifoaming agents.

The invention is further illustrated in the following non-limiting examples.

EXAMPLE 1

Wild oats (*Avena sativa*) is seeded at 50 kg/ha in a north/south direction in early May.

Harrington 2-row barley is seeded in an east-west direction at 91 kg/ha in mid-May. The row width is 18 cm. The seed is drilled in with an International harvester 2.6 meter drill to a depth of 5 cm.

All trials employ standard accepted weed science procedures. Applications are made with a $CO_2$-powered sprayer. Test design is a modified randomized complete block design with four replications. All applications are made post emergence to the weeds and crop.

The test solutions are prepared by tank mixing sufficient quantities of aqueous solutions and/or dispersions of the test compounds.

The treated plots are examined at intervals during the growing season and rated for percent control of wild oats and crop injury. The data listed is an average of the replicates for that treatment.

TABLE 1

| | 17 days after treatment | | |
|---|---|---|---|
| TREATMENT | RATE (kg a.i./ha) | CROP[1] | W.O.[2] |
| A. Control | | 0 | 0 |
| B. Difenzoquat | 0.850 | 0 | 71 |
| C. Fenoxaprop ethyl | 0.060 | 46 | 76 |
| D. Fenoxaprop ethyl | 0.100 | 76 | 81 |
| E. Difenzoquat and Fenoxaprop ethyl | 0.850 and 0.060 | 25 | 75 |
| F. Difenzoquat and Fenoxaprop ethyl | 0.850 and 0.100 | 34 | 71 |

[1]Crop injury in percent
[2]Wild oat control in percent

TABLE 2

| | 34 days after treatment | | |
|---|---|---|---|
| TREATMENT | RATE (kg a.i./ha) | CROP[1] | W.O.[2] |
| A. Control | | 0 | 0 |
| B. Difenzoquat | 0.850 | 0 | 90 |
| C. Fenoxaprop ethyl | 0.060 | 31 | 73 |
| D. Fenoxaprop ethyl | 0.100 | 89 | 80 |
| E. Difenzoquat and Fenoxprop ethyl | 0.850 and 0.060 | 11 | 90 |
| F. Difenzoquat and Fenoxaprop ethyl | 0.850 and 0.100 | 27 | 90 |

[1]Crop injury in percent
[2]Wild oat control in percent

TABLE 3

| | 67 days after treatment | | |
|---|---|---|---|
| TREATMENT | RATE (kg a.i./ha) | CROP[1] | W.O.[2] |
| A. Control | | 0 | 0 |
| B. Difenzoquat | 0.850 | 0 | 99 |
| C. Fenoxaprop ethyl | 0.060 | 30 | 19 |
| D. Fenoxaprop ethyl | 0.100 | 94 | 63 |
| E. Difenzoquat and Fenoxaprop ethyl | 0.850 and 0.060 | 8 | 99 |
| F. Difenzoquat and Fenoxaprop ethyl | 0.850 and 0.100 | 15 | 97 |

[1]Crop injury in percent
[2]Wild oat control in percent

EXAMPLE 2

Following essentially the same procedure as in EXAMPLE 1, Katepwa Spring Wheat is planted with greenfoxtail (*Setaria viridis*) weeds. The results listed in TABLE 4 show that the combination of difenzoquat and fenoxaprop ethyl is very effective against greenfoxtail and is safe for the wheat crop.

TABLE 4

| | 34 days after treatment | | |
|---|---|---|---|
| TREATMENT | RATE (kg a.i./ha) | CROP[1] | G.F.[2] |
| A. Control | | 0 | 0 |
| B. Difenzoquat | 0.700 | 0 | 0 |
| C. Fenoxaprop ethyl | 0.060 | 0 | 85 |
| D. Fenoxaprop ethyl | 0.100 | 0 | 95 |
| E. Difenzoquat and Fenoxaprop ethyl | 0.700 and 0.060 | 0 | 95 |
| F. Difenzoquat and Fenoxaprop ethyl | 0.700 and 0.100 | 0 | 94 |

[1]Crop injury in percent
[2]Greenfoxtail control in percent

What is claimed is:

1. A herbicidal composition for controlling undesirable plant species, selected from the group consisting of wild oats, green foxtail and combinations thereof which are growing in barley comprising a fenoxaprop ethyl in combination with a difenzoquat salt wherein said composition protects said crop from injury.

2. The composition according to claim 1 wherein the difenzoquat is difenzoquat methyl sulfate.

3. A method for controlling undesirable plant species, selected from the group consisting of wild oats, green foxtail and combinations thereof which are growing in the presence of barley, which comprises applying to the locus in which said barley is growing a herbicidally effective amount of fenoxaprop ethyl and a difenzoquat salt, wherein the herbicidal combination is safe for said barley.

4. A method for protecting barley from injury by fenoxaprop ethyl which comprises applying a difenzoquat salt with the fenoxaprop ethyl in a non-phytotoxic antidotal amount.

5. The method according to claim 4 wherein the fenoxaprop ethyl is applied post-emergence.

6. The method according to claim 5 wherein the difenzoquat salt is difenzoquat methyl sulfate.

7. The method according to claim 6 wherein the difenzoquat methyl sulfate is applied at a rate of about 0.700 kg/ha to 0.850 kg/ha and the fenoxaprop ethyl is applied at a rate of about 0.060 kg/ha to 0.100 kg/ha.

* * * * *